(12) United States Patent
de Keyzer et al.

(10) Patent No.: US 7,582,230 B2
(45) Date of Patent: Sep. 1, 2009

(54) LIQUID CRYSTAL DISPLAY AND COLOUR FILTER WITH IMPROVED TRANSPARENCY FOR GREEN LIGHT

(75) Inventors: Gerardus de Keyzer, Riehen (CH); Taher Yousaf, Basel (CH); Vadiraj Subbanna Ekkundi, Mumbai (IN); Chandrasekhar Dayal Mudaliar, Mumbai (IN)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 466 days.

(21) Appl. No.: 10/523,742

(22) PCT Filed: Aug. 5, 2003

(86) PCT No.: PCT/EP03/08654

§ 371 (c)(1),
(2), (4) Date: Feb. 2, 2005

(87) PCT Pub. No.: WO2004/018477

PCT Pub. Date: Mar. 4, 2004

(65) Prior Publication Data

US 2006/0060829 A1   Mar. 23, 2006

(30) Foreign Application Priority Data

Aug. 14, 2002   (IN) .................. 600/MAS/2002

(51) Int. Cl.
*F21V 9/08*   (2006.01)
*C02B 27/00*   (2006.01)
*C09B 47/04*   (2006.01)

(52) U.S. Cl. .................. 252/582; 252/519.21; 250/225; 359/577; 540/139; 540/140

(58) Field of Classification Search ................. 252/582, 252/519.21, 519.5, 521.2; 250/225; 359/577; 540/139, 140
See application file for complete search history.

(56) References Cited

U.S. PATENT DOCUMENTS 3,853,783 A * 12/1974 Tucker ...................... 252/582
2002/0045111 A1 * 4/2002 Machiguchi et al. ........... 430/7

OTHER PUBLICATIONS

Hu, Mougang et al., "Hydroxyphthalocyanines as Potential Photodynamic Agents for Cancer Therapy", Journal of Medicinal Chemistry (1998), 41(11), 1789-1802.*
Rager, Christine et al.: Influence of Substituents, "Reaction Conditions and Central Metals on the Isomer Distributions of 1(4)-tetrasubstituted phthalocyanines", Chemistry—A European Journal (1999), 5(1), 280-288.*
Ruf, Michael et al.: "Silicon and Zinc Coordination to Peripheral Catechol Sites of (2,3,9,10,17,17,23,24-Octahydroxyphthalocyaninato)nickel(II). Phthalocyanine Coordination Chemistry at the Edge", Inorganic Chemistry (1998), 37(8), 1992-1999.*
Guo, L. et al.: "Ligand Substitution Effect on Optical Properties in Conducting Tetraazaporphyrines", Materials Research Society Symposium Proceedings, Materials Research Society, Pittsburg, PA, US, vol. 393, 1995, pp. 137-142.*
M. P. Somashekarappa et al, "Synthesis and Structural Studies on 1,8,15,22-Tetrahydroxy Phthalocyanines of Co(II), Ni(II), Cu(II) and Zn(II)", Oriental Journal of Chemistry, vol. 15(1), 1999, 65-70.*

* cited by examiner

*Primary Examiner*—Timothy J Kugel
(74) *Attorney, Agent, or Firm*—Joseph C. Suhadolnik

(57) ABSTRACT

The invention relates to novel liquid crystal displays comprising a broad backlight emission around 530 nm and a green color filter containing a phthalocyanine colorant, most adequately tetrahydroxy- or tetraalkoxy-substituted but lacking solubilizing groups.

14 Claims, No Drawings

LIQUID CRYSTAL DISPLAY AND COLOUR FILTER WITH IMPROVED TRANSPARENCY FOR GREEN LIGHT

The invention relates to novel liquid crystal displays comprising a broad backlight emission around 530 nm and a green colour filter containing a phthalocyanine colorant, most adequately tetrahydroxy- or tetraalkoxy-substituted but lacking solubilizing groups.

Tetrahydroxy-phthalocyanines and their electronic spectra are known from Can. J. Chem. 72, 1990-1998 [1994] and Orient. J. Chem. 15/1, 65-70 [1999]. There is no mention of colour filters, nor of liquid crystal displays.

Polyoxy-substituted phthalocyanines are known from WO 88/06175, EP 0 934 985 and EP 1 072 959, which are used as Langmuir-Blodgett films and IR-absorbers, respectively. Their absorption maxima are at 734 nm or above.

EP 0 833 203 discloses a photosensitive resin formulation for colour filters comprising phthalocyanines with one to eight alkoxy or phenoxy groups, the remainder positions on the chromophore being perhalogenated. For green filters, it is teached that the core metal should be a tetravalent metal possessing a ligand such as $SnCl_2$, TiO or in particular VO (page 27). The presence of fluorine is important, too. However, tetraphenoxy-dodecafluoro dichlorotin(IV) phthalocyanine has insatisfactory properties (table 13) and there are no data for the single disclosed alkoxy derivative tetrabutoxy-dodecafluoro titanyl phthalocyanine.

Tetroxy-substituted phthalocyanines are known from EP 0 519 423, EP 0 546 856/U.S. Pat. No. 6,306,550, EP 0 896 033, JP 07/286108A, JP 07/286109A, JP 09/279050A and JP 08/291261A for use in colour filters and/or in optical recording media. Further, JP 2002/212471A relates to an ink for making colour filters comprising tetraphenoxy- or tetraphenylthio-substituted phthalocyanines in combination with a xanthene or azo pyrazolone dye. All these compounds are highly soluble (due to the presence of solubilizing groups and asymmetric centers leading to optical isomery), leading to undesired migration especially under heat from backlight. Their absorption maxima are above 680 nm, with only broad and low side absorptions from 600 to 650 nm. The transmittance for green light and light stability are not entirely satisfactory either.

EP 0 633 296 discloses highly soluble dyestuffs having excellent transmittance characteristics in colour filters. Amongst other chromophores, phthalocyanines are also disclosed. However, the hindered aryloxy groups (bisphenolic) lead to a much too hypsochromic transmittance maximum, which lies below 500 nm (examples 7 and 8, FIGS. 10 and 11).

WO-02/095791 relates to a liquid crystal picture screen with white light source; it has a priority of May 23, 2001 and was published on Nov. 28, 2002. There is no indication on the green filter's pigmentation.

The purpose of the invention is to provide a liquid crystal display having a better transmittance for green light and efficient absorption for red light (particularly from 600-620 nm), with a steep slope between green and red as well as good light stability.

The invention pertains to a colour filter comprising areas of at least three different colours, wherein at least one area has its maximal visible light transmittance at a wavelength of from 520 to 540 nm and comprises a compound of formula

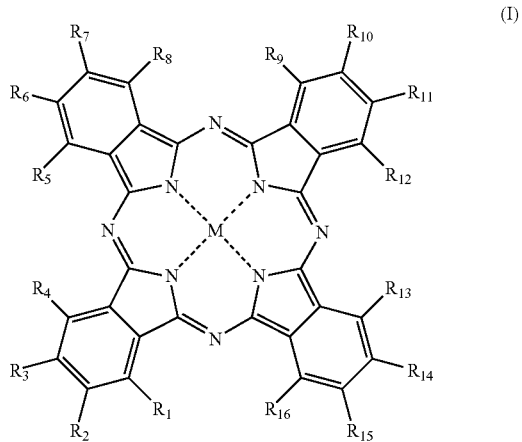

dispersed in a high molecular weight material, in which formula (I) $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$ and $R_{16}$ are each independently from the others selected from the group consisting of H, F, Cl, Br, OH and

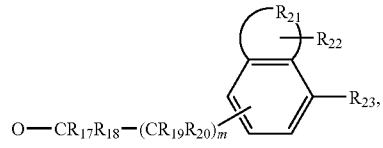

$R_{17}$, $R_{18}$, $R_{19}$ and $R_{20}$ are independently from the others H or F, m is 0 or 1, $R_{21}$ is 2H, $(CH_2)_3$, $(CH_2)_4$, $(CH)_4$, $(CH)_2CH_2$, $(CH)_2(CH_2)_2$ or $CH_2(CH)_2CH_2$, $R_{22}$ and $R_{23}$ are independently from each other H, OH, Cl, $NO_2$, $CONHR_{24}$ or $NHCOR_{24}$, $R_{24}$ is methyl, ethyl or n-propyl, and M is 2 H, Cu, Co, Ni or Zn, with the proviso that one of $R_1$, $R_2$, $R_3$ and $R_4$, none or one of $R_5$, $R_6$, $R_7$ and $R_8$, none or one of $R_9$, $R_{10}$, $R_{11}$ and $R_{12}$, and none or one of $R_{13}$, $R_{14}$, $R_{15}$ and $R_{16}$ are selected from the group consisting of OH and

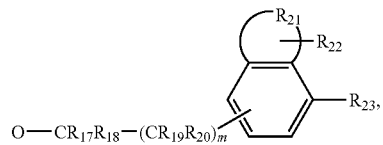

and all other $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, and $R_{16}$ are selected from the group consisting of H, F, Cl and Br.

The compound of formula (I) has preferably from 2 to 4, particularly preferred 4 of the substituents $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$ and $R_{16}$ selected from the group consisting of OH and

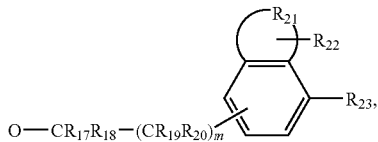

with particular preference

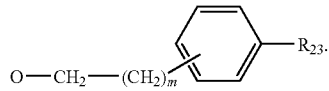

The other substituents $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$ and $R_{16}$ are preferably selected from the group consisting of H, F and Cl; particularly preferred, at least 8 of these other substituents are all H. Most preferred, $R_3$, $R_4$, $R_5$, $R_6$ and either $R_9$, $R_{10}$, $R_{15}$ and $R_{16}$ or $R_{11}$, $R_{12}$, $R_{13}$ and $R_{14}$ are selected from the group consisting of H, F and Cl, and in particular are H.

$R_{17}$, $R_{18}$ $R_{19}$ and $R_{20}$ are preferably identical, with particular preference all H. m is preferably 0. $R_{23}$ is preferably H. $R_{24}$ is preferably methyl. M is preferably Cu, Co, Ni or Zn, with particular preference Cu. The instant compounds of formula (I) are partially known, partially new. Those which are new can be made easily in analogy to known methods. It is possible to use the instant compounds pure or as mixtures, for example but not limited to mixtures of isomers. Normally, the isomers will be positional isomers, as the instant formula generally does not allow optical isomers excepted such resulting from asymmetric but nearly isogeometric mixed substitution by fluorine and hydrogen as $R_{17}$, $R_{18}$, $R_{19}$ and $R_{20}$. Plane symmetry is instantly preferred because, surprisingly, it appears to promote the pigmentary properties and to decrease too high solubility. Especially preferred are phthalocyanines wherein the chromophore is in one symmetry plane, with a second symmetry plane perpendicular to the first symmetry plane, optionally also with a third symmetry plane perpendicular to the first two, in particular phthalocyanines wherein $R_1$, $R_8$, $R_{12}$ and $R_{13}$, $R_2$, $R_7$, $R_{11}$ and $R_{14}$, $R_1$, $R_8$, $R_9$, or $R_2$, $R_7$, $R_{10}$ and $R_{15}$ are hydroxy or aralkyloxy groups, and the remaining $R_1$ to $R_{16}$ are halogen or hydrogen, preferably hydrogen such as in following compounds:

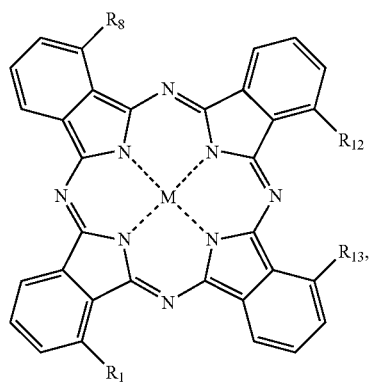

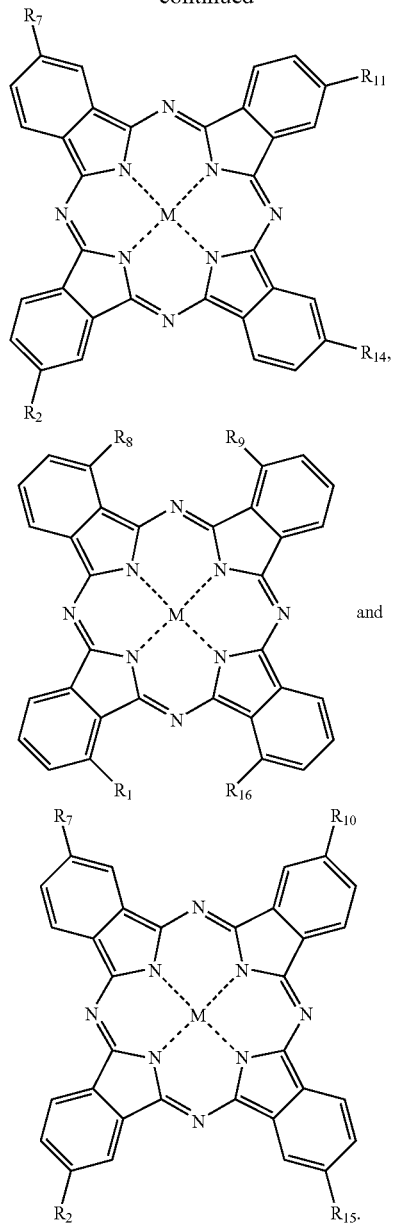

When mixtures are used, it is preferable that the mixtures comprise at least 30% by weight, in particular at least 40% by weight, with particular preference at least 50% by weight of such especially preferred isomers.

Thus, the invention also pertains to a compound of formula (I), with the proviso that said compound is not a 1,8,15,22-, 2,9,16,23-, 2,9,16,24-, 2,9,17,24- or 2,10,16,24-tetrahydroxy phthalocyanine.

The instant colour filter is particularly suitable for use together with light sources such as known from cathode ray (CRT) or preferably neon tubes but hitherto not used in liquid crystal displays (LCD). The results are excellent, with greatly increased light transmittance for red light as well as outstanding colorant light stability. It is possible to get a high colour gamut, especially enabling to match the NTSC standard with excellent transparency and transmittance.

Hence, the invention also pertains to a liquid crystal display comprising a colour filter as defined above and a luminescent backlight source emitting green light, from 90 to 100 energy-% of which green light has a wavelength of from 500 to 560 nm.

Preferably, the emitted green light has a maximum luminescence intensity in the wavelength range from 522 to 538 nm. The maximum luminescence has preferably a half band width of at least 8 nm, with particular preference a half band width of at least 15 nm, most preferred a half band width of at least 25 nm. The half band width is the wavelength range within which the visible luminescence intensity reaches 50% or more of the maximum visible luminescence intensity.

Suitable light sources are known per se from the different fields of cathode ray or neon tubes, for example as P1 (see Mori, Kakitani, Miyake, Yamaguchi, Okayama University of Science, Japan, Okayama Rika Daigaku Kiyo A [1994], 30A, 115-120) with a maximum visible luminescence intensity around 530 nm. Suitable light sources may in particular comprise $Zn_2SiO_4$: Mn as luminescence source, which might be powered for example by UV light or by bombardment with electrons. However, the skilled artisan will obviously also try light sources having similar or better performance. In contrast, luminescent light sources hitherto used in liquid crystal displays (for example such based on La, Ce, Tb, Yb, Eu, Ho and/or Dy, like F10) have a very narrow maximum emission at a wavelength around 545 nm, with undesired narrow side emissions at 485 and 580 nm. Generally, the instant green light source will be combined with other light sources, such as each a blue and a red light source, in order the whole combination to emit white light. The prior art liquid crystal display technology and light sources used therein is well-known from many books, publications and patents; to cite just few examples see U.S. Pat. No. 6,280,890 or the prior art documents discussed above, all contents of which are incorporated in the instant application by reference, or also Colour filters for LCD's, Displays 14(2), 115-124 [1993].

Of course, it is also possible to use phthalocyanines of equivalent spectral properties instead of the instant compounds of formula (I), especially in applications with less demanding quality requirements. Thus, the invention also pertains to a liquid crystal display comprising: a colour filter comprising areas of at least three different colours, wherein at least one area has its maximal visible light transmittance at a wavelength of from 520 to 540 nm, preferably from 520 to 530 nm, and comprises a phthalocyanine compound; and a luminescent backlight source emitting green light, from 90 to 100 energy-% of which green light has a wavelength of from 500 to 560 nm.

Colours have a chroma C* of at least 10 (C.I.E. L*C*h 1976 colour space); different colours have a hue difference Δh of from 30 to 330. Usually, colour filters have transparent blue, green and red areas and optionally hiding black areas, all arranged in regular pattern. Transparent areas generally have a transparency of from 70 to 100% (preferably from 85 to 100%), hiding areas a transparency of from 0 to 69% (preferably from 0 to 30%). Visible light is of wavelength from 400 to 700 nm, with each a blue component (wavelength from 400 to 500 nm), a green component (wavelength from 500 to 600 nm) and a red component (wavelength from 600 to 700 nm).

The invention further pertains to the use of an instant colour filter in a liquid crystal display.

It is believed that the surprising improvement is at least in great part due to the quite pigmentary properties of the compounds of formula (I).

Hence, the skilled artisan will obviously recognize that the instant compounds of formula (I) are useful for pigmenting high molecular weight organic material in the mass, too, There are many possible applications in all fields where organic pigments are used, such as inks, coatings and polymers. The instant compounds will prove particularly useful in combination with fine or transparent pigments, as well as in applications requiring an elevated temperature or wherein the thermal colour stability is an issue. Typical examples are coil- and powder coatings, extruded or injection moulded engineering plastics as well as melt-spun fibers, this list self-evidently not being exhaustive.

The high molecular mass organic material to be coloured in accordance with the invention may be natural or synthetic in origin and normally has a molecular weight in the range from $10^3$ to $10^8$ g/mol. The said material may, for example, comprise natural resins or drying oils, rubber or casein, or modified natural substances, such as chlorinated rubber, oil-modified alkyd resins, viscose, cellulose ethers or esters, such as cellulose acetate, cellulose propionate, cellulose acetobutyrate or nitrocellulose, but especially fully synthetic organic polymers (both thermosets and thermoplastics), as obtained by addition polymerization, polycondensation or polyaddition, examples being polyolefins such as polyethylene, polypropylene or polyisobutylene, substituted polyolefins such as polymers of vinyl chloride, vinyl acetate, styrene, acrylonitrile or acrylates and/or methacrylates or butadiene, and also copolymers of the abovementioned monomers, especially ABS or EVA.

From the series of the polyaddition resins and polycondensation resins, mention may be made of the condensates of formaldehyde with phenols, known as phenolic resins, and the condensates of formaldehyde with urea, thiourea and melamine, known as amino resins, the polyesters used as paint resins, and indeed both saturated resins, such as alkyd resins, and unsaturated resins, such as maleate resins, and also the linear polyesters and polyamides, or silicones.

The high molecular mass compounds mentioned may be present individually or in mixtures, as plastic masses or melts, which may if desired be spun into fibres.

They may also be present in the form of their monomers or in the polymerized state in dissolved form as film formers or binders for coating materials or printing inks, such as linseed oil varnish, nitrocellulose, alkyd resins, melamine resins, urea-formaldehyde resins or acrylic resins. When used in coatings together with the instant compositions, pigments exhibit higher fastnesses than the chemically identical pigments of similar mean particle size or of similar surface area. However, their use in coatings is relatively limited due to their high transparency (for example in metallic finishes).

Pigmentation of the high molecular mass organic substances with compounds of formula (I) takes place, for example, by mixing one or more compounds of formula (I), in the form if desired of masterbatches, into these substrates using roll mills, mixers or milling apparatus. In general, the pigmented material is subsequently brought into the desired ultimate form by techniques known per se such as calendering, compression moulding, extrusion, spreading, casting or injection moulding. In order to produce nonrigid mouldings or to reduce their brittleness it is often desirable to incorporate what are known as plasticizers into the high molecular mass compounds prior to their shaping. Examples of such plasticizers which may be used are esters of phosphoric acid, phthalic acid or sebacic acid. In the process of the invention, the plasticizers may be incorporated before or after the incorporation of the pigmentary colorant into the polymers. A further possibility, in order to obtain different hues, is to add fillers and/or other colouring constituents such as white, coloured or black pigments, and also effect pigments, in the particular desired amount to the high molecular mass organic materials in addition to the compounds of formula (I).

For pigmenting coating materials and printing inks, the high molecular mass organic materials and the compounds of formula (I), alone or together with additives such as fillers, other pigments, siccatives or plasticizers, are finely dispersed or dissolved in, generally, an organic and/or aqueous solvent or solvent mixture. One possible procedure here is to disperse or dissolve the individual components alone, or else two or more together, and only then to combine all of the components.

A further embodiment therefore additionally provides a mass-coloured high molecular mass organic material comprising
(i) from 0.05 to 70% by weight, based on the sum of (i) and (ii), of a compound of formula (I); and
(ii) from 99.95 to 30% by weight, based on the sum of (i) and (ii), of a high molecular mass organic material.

Said material comprises both a ready-to-use composition or an article formed therefrom, and a masterbatch, in the form of granules, for example. If desired, the high molecular mass organic material coloured in accordance with the invention may also comprise customary additives, for example stabilizers.

A further embodiment therefore additionally provides a process for colouring high molecular mass organic material in the mass, which comprises incorporating therein a compound of formula (I), for example by mixing the high molecular mass organic material with the compound of formula (I), optionally in the form of a masterbatch, in a manner known per se and processing this mixture.

The instant compounds of formula (I) are particularly preferably used for pigmenting high molecular weight organic materials which are processed at high temperatures, for example at 200 to 350° C. Most preferably, they are used for pigmenting high molecular weight organic materials which are processed at 260 to 320° C.

It is well-known in the field which high molecular weight organic materials amongst the above-mentioned are processed at the above-mentioned high temperatures. Most frequently, this is the case for engineering plastics such as for example polyolefins, polyamides or ABS, which may be processed by injection moulding; for fiber materials which may be processed by melt spinning; and for special coating materials such as those used for powder coatings or coil coatings.

The invention in particular also pertains to the use of the instant pigments in colour filters, which can themselves be used for example in electro-optical systems such as TV screens, liquid crystal displays, charge coupled devices, plasma displays or electroluminescent displays and the like. These may be, for example, active (twisted nematic) or passive (supertwisted nematic) ferroelectric displays or light-emitting diodes.

The compounds of formula (I) will generally be used in the manufacture of colour filters as a dispersion in an organic solvent or water. There are several ways to manufacture these colour filters, which follow two mainstreams:
Direct patterning during applying;
Patterning after applying the colorant.

Direct patterning can be obtained by several printing techniques, such as impact (off-set, flexography, stamping, letter-press etc.) as well as non-impact (ink jet techniques).

Other direct patterning techniques are based on lamination processes, electronic discharging processes like electrodeposition and some special colour proofing methods, like the so-called Chromalin™ process (DuPont).

For impact printing techniques, the colorant may be dispersed in water or organic solvents by standard de-agglomeration methods (Skandex, Dynomill, Dispermat and the like) in the presence of a dispersant and a polymeric binder to produce an ink. Any dispersion technique known in the field, including the choice of solvent, dispersant and binder, can be used. The type of ink and its viscosity depend on the application technique and are well-known to the skilled artisan. Most usual binders, to which the invention is of course not limited, are (meth)acrylates, epoxies, PVA, polyimides, Novolak systems and the like as well as combinations of these polymers.

The ink dispersion then can be printed on all kind of standard printing machines. Curing of the binder system is preferably achieved by a heating process. The three colours can be applied at once or in different printing steps with intermediate drying and/or curing steps, for example one colour at the time in three printing steps.

Inks for use in ink jet, for example piezo or bubble jet, can be prepared likewise. They generally contain a colorant dispersed in water and/or one or a mixture of many hydrophilic organic solvents in combination with a dispersant and a binder.

For ink jet printing a standard ink jet printer can be used or a dedicated printer can be built in order to optimize for example the printing speed etc.

For lamination techniques, like thermal transfer and the like, a web system has to be made. The colorant is dispersed in a solvent or water with dispersant and binder and coated on a foil and dried. The colorant/binder system can be patternwise or uniformly transferred to a colour filter substrate with the help of energy (UV, IR, heat, pressure etc.). Depending on the technique used, the colorant for example may be transferred alone (dye diffusion or sublimation transfer), or the colorant dispersion may be entirely transferred including the binder (wax transfer).

For electrodeposition, the colorant has to be dispersed in water together with an ionized polymer. By means of an electrical current, the ionized polymer is deionized at the anode or the cathode and, being insoluble then, deposited together with the colorants. This can be done on patterned or patternwise shielded, by a photoresist, (transparent) photoconductors like ITO etc.

The Chromalin™ process makes use of a photosensitive material, deposited on a colour filter substrate. The material becomes tacky upon UV exposure. The so called 'toner', comprising a mixture or compound of colorant and polymer, is distributed on the substrate and sticks on the tacky parts. This process has to be done three to four times for R,G,B and eventually black.

Patterning after applying is a method based mostly on the known photoresist technology, wherein the colorant is dispersed in the photoresist composition. Other methods are indirect patterning with the help of a separate photoresist or lamination techniques.

The colorant may be dispersed into photoresists by any standard method such as described above for the printing processes. The binder systems may also be identical. Further suitable compositions are described for example in EP 0 654 711, WO 98/45756 or WO 98/45757.

Photoresists comprise a photoinitiator and a poly-crosslinkable monomer (negative radical polymerization), a material to crosslink the polymers itself (for example a photoacid generator or the like) or a material to chemically change the solubility of the polymer in certain developing media. This process, however, can also be done with heat (for example using thermal arrays or an NIR beam) instead of UV, in the case of some polymers which undergo chemical changes during heating processes, resulting in changes of solubility in the mentioned developing media. A photoinitiator is then not needed.

The photosensitive or heat sensible material is coated on a colour filter substrate, dried and UV (or heat) irradiated, sometimes again baked (photoacid generators) and developed with a developing medium (mostly a base). In this last step only the non-exposed (negative systems) or only the exposed (positive systems) parts are washed away, giving the wanted pattern. This operation has to be repeated for all the colours used.

Photosensitive lamination techniques are using the same principle, the only difference being the coating technique. A photosensitive system is applied as described above, however on a web instead of a colour filter substrate. The foil is placed on the colour filter substrate and the photosensitive layer is transferred with the help of heat and/or pressure.

Indirect processes, with the above mentioned polymeric binders without a photosensitive component, make use of an extra photoresist, coated on top of the colored resist. During the patterning of the photoresist, the colored resist is patterned as well. The photoresist has to be removed afterwards.

More details about the manufacture of colour filters can be found in text books, reviews and other scientific articles. The skilled artisan will associate the instant invention with the use of any such known technique as well.

For example, which is of course in no way limitative, substantially colourless methacrylic resin are commonly used in colour filters, examples thereof which are known to the skilled artisan being copolymers of aromatic methacrylates with methacrylic acid of $M_w$ from 30,000 to 60,000. Such resins are highly appropriated to make films by spin-coating.

The colour filters of the invention contain the colorants of formula (I) judiciously in a concentration of from 1 to 75% by weight, preferably from 5 to 50% by weight, with particular preference from 25 to 40% by weight, based on the overall weight of the colored layer. The instant green colored layer as well as each a blue and a red layer will generally be applied on a substrate which is preferably essentially colourless (T≧95% all over the visible range from 400 to 700 nm).

The invention therefore likewise provides a colour filter wherein the area which has its maximal visible light transmittance at a wavelength of from 520 to 540 nm comprises from 1 to 75% by weight, preferably from 5 to 50% by weight, with particular preference from 25 to 40% by weight, based on the overall weight of the area, of a compound of formula (I).

The instant printing inks or photoresists for making colour filters contain the compounds of formula (I) judiciously in a concentration of from 0.01 to 40% by weight, preferably from 1 to 25% by weight, with particular preference from 5 to 10% by weight, based on the overall weight of the printing ink or photoresist.

The invention therefore likewise provides a composition for making colour filters comprising from 0.01 to 40% by weight, preferably from 1 to 25% by weight, with particular preference from 5 to 10% by weight, based on the overall weight of the composition, of a compound of formula (I).

Preferred are instant compositions which additionally also comprise from 5 to 500 weight-% of a polymerisable compound, based on the compound of formula (I). Most preferred is from 50 to 200 weight-% of a polymerisable compound, based on the compound of formula (I). The polymerisable compound is suitably either liquid or dissolved in water and/or a liquid solvent of boiling point from 25 to 250° C., preferably of boiling point from 35 to 150° C.

This instant compositions also may additionally contain other colorants of different structure. The additional components can shift the mixture's spectrum hypsochromically or bathochromically depending on their own hue, or they can complement the absorption so as to suppress undesired transmission holes. A particular embodiment is the addition of a coloristically effective amount of a yellow colorant in order to decrease the transmission for blue light. The skilled artisan will appreciate by himself which colorants can additionally be used, and in which amounts, depending on the desired result. Particularly preferred yellow colorants are those disclosed in WO 02/34839 and EP-2001-01811024.7, the entire contents of which are incorporated herein by reference.

In certain cases, it is advantageous to add to the inventive compositions other additives such as wetting agents, surfactants, defoamers, antioxidants, UV absorbers, light stabilizers, plastisizers, or general texture improving agents and so forth. Generally such additives can be used in a concentration from about 0.1 to 25 percent, preferably from about 0.2 to 15% and most preferably from about 0.5 to 8%, by weight based on the total weight of the inventive compositions.

Suitable surfactants include anionic surfactants such as alkylbenzene- or alkylnaphthalene-sulfonates, alkylsulfosuccinates or naphthalene formaldehyde sulfonates; cationic surfactants including, for example, quaternary salts such as benzyl tributyl ammonium chloride; or nonionic or amphoteric surfactants such as polyoxyethylene surfactants and alkyl- or amidopropyl betaines, respectively.

Suitable texture improving agents are, for example, fatty acids such as stearic acid or behenic acid, and fatty amines such as laurylamine and stearylamine. In addition, fatty alcohols or ethoxylated fatty alcohols, polyols such as aliphatic 1,2-diols or epoxidized soy bean oil, waxes, resin acids and resin acid salts may be used for this purpose.

Suitable UV stabilizers are, for example, the known benzotriazole derivatives known under the trade name TINUVIN® or CIBA® Fast H Liquid an aryl sulfonated benzotriazol, both being products of CIBA Specialty Chemicals Corporation.

The following examples further describe some preferred embodiments of the invention, but do not limit the scope of the invention. In the examples, all parts are by weight unless otherwise indicated.

EXAMPLE 1

A 1 liter round-bottomed flask equipped with a magnetic stirrer, reflux condenser, and a thermometer is charged with 100 g of the product obtained 5 according to example 2 of EP 0 703 280 and 400 ml of trifluoroacetic acid, and heated to reflux. 20 ml of water are then added and the solution left to reflux overnight at about 90° C. The reaction mixture is then cooled to room temperature and poured into 3000 ml of water. The resulting bright green suspension is stirred for about 1 hour, then filtered. The resulting product is washed with 500 ml of water followed by 500 ml of cold acetone, then air-dried to yield pure tetra-α-hydroxy copper phthalocyanine yield: 87% of theory).

EXAMPLE 2

100 g of 4-benzyloxy phthalodinitrile, 52 g of urea, 14.4 g of anhydrous copper (II) chloride and 2 g of ammonium molybdate in about 350 ml of nitrobenzene are mixed in a 1000 ml glass reactor. The reaction mixture is gradually heated from 80° C. to about 140° C. in about 34 hours, then to 160° C. for another hour. After a total of 6 hours, the reaction mixture is cooled to 50° C., then 1000 ml of methanol are added and the reaction mixture is stirred vigorously for ½ hour and then filtered. The green solid obtained is then washed with 200 ml of methanol followed by 1000 ml of water to remove any water-soluble impurities and finally with 500 ml of acetone to remove any colored impurities. The solid is dried at 60° C./2·10³ Pa. 90 g of 2,9,16,23-tetra-benzyloxy copper phthalocyanine are obtained, the UV-VIS spectrum of which in N-methyl-pyrrolidone shows iabsorption maxima ($\lambda_{max}$) at 347 nm ($\epsilon$=62800), 614 nm ($\epsilon$=34400) and 681 nm ($\epsilon$=132300).

EXAMPLE 3

100 g of 3-benzyloxy phthalodinitrile, 62 g of urea, 14.4 g of anhydrous copper (II) chloride and 2 g of ammonium molybdate in about 500 ml of nitrobenzene are mixed in a 1000 ml glass reactor. The reaction mixture is gradually heated from 80° C. to about 140° C. in about 34 hours, during which time the colour of the solution slowly turns green. The reaction is then heated to 160° C. and kept at this temperature for another hour. After a total of 6 hours, the reaction mixture is cooled to 50° C. then 1000 ml of methanol are added and the reaction mixture is stirred vigorously for ½ hour and then filtered. The green solid obtained is washed with 1000 ml of methanol followed by 2000 ml of water to remove any water-soluble impurities and finally with 300 ml of acetone to remove any colored impurities. The solid is dried at 60° C./2·10³ Pa. 95 g of 1,8,15,22-tetra-benzyloxy copper phthalocyanine are obtained, the UV-VIS spectrum of which in N-methylpyrrolidone shows iabsorption maxima ($\lambda_{max}$) at 351 nm ($\epsilon$=36100), 633 nm ($\epsilon$=31300) and 708 nm ($\epsilon$=144200).

EXAMPLE 4

25 g of 3-benzyloxy phthalodinitrile, 75 g of 4-benzyloxy phthalodinitrile, 52 g of urea, 14.4 g of anhydrous copper (II) chloride and 2 g of ammonium, molybdate in about 500 ml of nitrobenzene are mixed in a 1000 ml glass reactor. The reaction mixture is gradually heated from 80° C. to about 140° C. in about 3-4 hours, during which time the colour of the solution turns green. The reaction is then heated to 160° C. and kept at this temperature for another hour. After a total of 6 hours, the reaction mixture is cooled to 50° C. then 1500 ml of methanol are added and the reaction mixture is stirred vigorously for ½ hour and then filtered. The green solid obtained is washed with 1000 ml of methanol followed by 1500 ml of water to remove any water-soluble impurities and finally with 500 ml of acetone to remove any colored impurities. The solid is dried at 60° C./2·10³ Pa. 90 g of an isomeric mixture of tetra-benzyloxy copper phthalocyanine isomers are obtained.

EXAMPLE 5

(a) 1 Kg pigment of structure

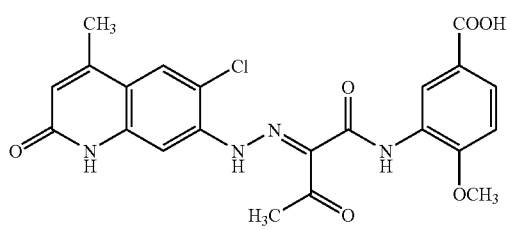

(prepared according to WO 02/34839) and 4 Kg of sodium chloride are dry-milled in a 10 l mixer (FM 10 MB™, Henschel, Germany) for one hour at 3200 rpm (propeller diameter 220 mm).

(b) A laboratory kneader with a capacity of 1 l is charged with 42 g of the pigment from example 1, 40 g of the product according to example 5 (a), 168 g of sodium chloride and 45 ml of diacetone alcohol and the rotary speed is set to 100 rpm. The walls of the kneader are cooled to 30° C. so that the temperature in the mass does not exceed 40-45° C. After 8 hours, 150 ml of deionized water are added slowly, the resulting mixture is discharged onto a Buchner funnel and the material in the funnel is washed with water until the washing water is salt-free. The product is dried for 15 hours at 80° C./3·10³ Pa, then sieved through a sieve with a mesh size of 0.4 mm.

(c) In a 100 ml glass vessel containing 78.3 g of zircon ceramic beads, 2.52 g of the product from (b), 0.28 g of Solsperse® 22,000 (Avecia), 0.56 g of Solsperse® 24,000 (Avecia) and 12.65 g of propylene glycol monomethyl ether acetate (MPA, CAS Reg. No 108-65-6) are stirred at 20° C. with a Dispermat™ at 1000 rpm for 10 minutes and at 3000 rpm for 180 minutes. Following the addition of 5.45 g of acrylic polymer binder (as a 35% solution in MPA) at room temperature, stirring is continued at 3000 rpm for 30 minutes. After the beads have been separated off, the dispersion is diluted with an equal amount of MPA. A glass substrate (Corning Type 1737-F) is coated with this dispersion in a spin-coating apparatus and is spun at 1000 rpm for 30 s. The drying of the coat is carried out at 100° C. for 2 minutes and at 200° C. for 5 minutes on a hotplate. A bright pure green coating with a very sharp transmission maximum at 525-530 nm is obtained.

EXAMPLE 6

A neon tube is made by standard methods, comparable with the neon backlight F10 (Toshiba) or the C86 (Philips), with the difference that the standard terbium containing luminescent material is replaced by $Zn_2SiO_4$: Mn. With this backlight and the green colour filter of example 5, the colour point is measured with a standard measuring method. The Y-value is high and x as well as y are very close to the NTSC target (0.210/0.710).

EXAMPLES 7-9

The procedure of examples 5 (a), (b) (c) and (6) is used, but with the difference that in step (a) the products according to example 2 to 4 are used instead of the product according to example 1. Similar results are obtained.

The invention claimed is:

1. A colour filter comprising areas of at least three different colours, wherein at least one area has its maximal visible light transmittance at a wavelength of from 520 to 540 nm and comprises a pigmentary compound of formula

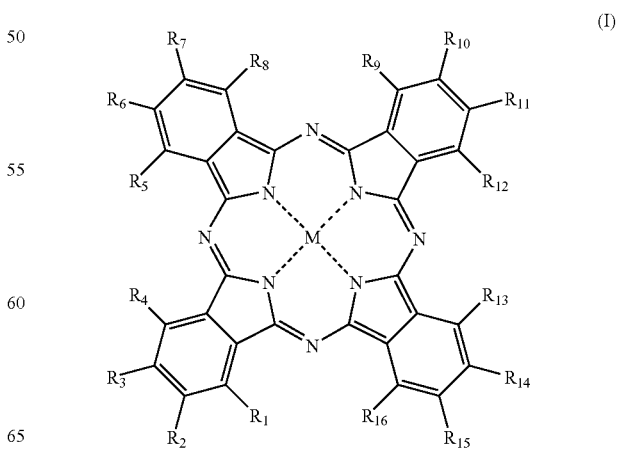

dispersed in a high molecular weight material,
in which formula (I) $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$ and $R_{16}$ are each independently from the others selected from the group consisting of H, OH and

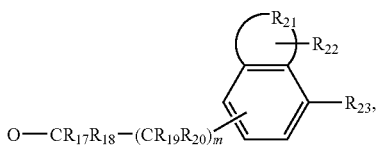

$R_{17}$, $R_{18}$, $R_{19}$ and $R_{20}$ are H, m is 0 or 1,
$R_{21}$ is 2 H, $(CH_2)_3$, $(CH_2)_4$, $(CH)_4$, $(CH)_2CH_2$, $(CH)_2(CH_2)_2$ or $CH_2(CH)_2CH_2$,
$R_{22}$ and $R_{23}$ are independently from each other H, OH, $NO_2$, $CONHR_{24}$ or $NHCOR_{24}$, $R_{24}$ is methyl, ethyl or n-propyl, and
M is 2 H, Cu, Co or Ni,
with the proviso that one of $R_1$, $R_2$, $R_3$ and $R_4$, none or one of $R_5$, $R_6$, $R_7$ and $R_8$, none or one of $R_9$, $R_{10}$, $R_{11}$ and $R_{12}$, and none or one of $R_{13}$, $R_{14}$, $R_{15}$ and $R_{16}$ are selected from the group consisting of OH and

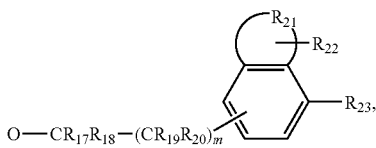

and all other $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$ and $R_{16}$ are H.

2. A composition for making colour filters comprising from 0.01 to 40% by weight, based on the overall weight of the composition, of a compound of formula (I) according to claim 1.

3. A composition according to claim 2, which additionally comprises from 5 to 500 weight-% of a polymerisable compound, based on the compound of formula (I).

4. A composition for making colour filters according to claim 3, comprising from 1 to 25% by weight, based on the overall weight of the composition, of a compound of formula (I).

5. A composition for making colour filters according to claim 3, comprising from 5 to 10% by weight, based on the overall weight of the composition, of a compound of formula (I).

6. A compound of formula (I) according to claim 1, with the proviso that said compound is not a 1,8,15,22-, 2,9,16,23-, 2,9,16,24-, 2,9,17,24- or 2,10,16,24-tetrahydroxy phthalocyanine.

7. A mass-coloured high molecular mass organic material comprising
   (i) from 0.05 to 70% by weight, based on the sum of (i) and (ii), of a compound of formula (I) according to claim 6; and
   (ii) from 99.95 to 30% by weight, based on the sum of (i) and (ii), of a high molecular mass organic material.

8. A liquid crystal display comprising a colour filter according to claim 1 and a luminescent backlight source emitting green light, from 90 to 100 energy-% of which green light has a wavelength of from 500 to 560 nm.

9. A liquid crystal display comprising a colour filter according to claim 1.

10. A colour filter according to claim 1, wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$ and $R_{16}$ are selected from the group consisting of H, OH and

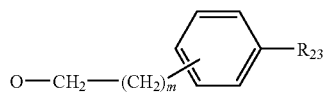

and each one of $R_1$, $R_2$, $R_3$ and $R_4$, one of $R_5$, $R_6$, $R_7$ and $R_8$, one of $R_9$, $R_{10}$, $R_{11}$ and $R_{12}$, and one of $R_{13}$, $R_{14}$, $R_{15}$ and $R_{16}$ are selected from the group consisting of OH and

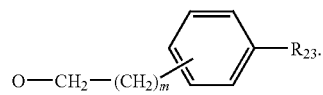

11. A colour filter according to claim 1, wherein the area which has its maximal visible light transmittance at a wavelength of from 520 to 540 nm comprises from 1 to 75% by weight, based on the overall weight of the area, of a compound of formula (I).

12. A colour filter according to claim 1, further comprising a yellow colorant.

13. A colour filter according to claim 1, wherein the area which has its maximal visible light transmittance at a wavelength of from 520 to 540 nm comprises from 5 to 50% by weight, based on the overall weight of the area, of a compound of formula (I).

14. A colour filter according to claim 1, wherein the area which has its maximal visible light transmittance at a wavelength of from 520 to 540 nm comprises from 25 to 40% by weight, based on the overall weight of the area, of a compound of formula (I).

* * * * *

UNITED STATES PATENT AND TRADEMARK OFFICE
CERTIFICATE OF CORRECTION

PATENT NO. : 7,582,230 B2 Page 1 of 1
APPLICATION NO. : 10/523742
DATED : September 1, 2009
INVENTOR(S) : de Keyzer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 904 days.

Signed and Sealed this

Fourteenth Day of September, 2010

David J. Kappos
*Director of the United States Patent and Trademark Office*